(12) United States Patent
Downs et al.

(10) Patent No.: US 9,398,867 B2
(45) Date of Patent: Jul. 26, 2016

(54) EFFICIENT ACTIVITY CLASSIFICATION FROM MOTION INPUTS

(71) Applicant: Archinoetics, LLC., Honolulu, HI (US)

(72) Inventors: J. Hunter Downs, Honolulu, HI (US);
Nathan Ronald Kowahl, Honolulu, HI (US); Fahrettin Olcay Cirit, San Francisco, CA (US); William James Robinson, Waipahu, HI (US); Richard Moffitt Cowan, Honolulu, HI (US)

(73) Assignee: ARCHINOETICS LLC, Honolulu, HI (US)

( * ) Notice: Subject to any disclaimer, the term of this patent is extended or adjusted under 35 U.S.C. 154(b) by 114 days.

(21) Appl. No.: 14/148,678

(22) Filed: Jan. 6, 2014

(65) Prior Publication Data

US 2014/0195538 A1  Jul. 10, 2014

Related U.S. Application Data

(60) Provisional application No. 61/749,494, filed on Jan. 7, 2013.

(51) Int. Cl.
*G06F 17/00* (2006.01)
*A61B 5/11* (2006.01)
(52) U.S. Cl.
CPC ............. *A61B 5/1123* (2013.01); *A61B 5/1118* (2013.01); *A61B 2562/0219* (2013.01)

(58) Field of Classification Search
CPC . G06Q 10/08; G06Q 10/083; G06Q 10/0833; G06F 19/00; G06F 3/0346; G06F 3/017
See application file for complete search history.

(56) References Cited

U.S. PATENT DOCUMENTS

2012/0197322 A1* 8/2012 Skelton ................ A61N 1/3787
607/2

* cited by examiner

*Primary Examiner* — Truong Vo

(57) ABSTRACT

A device worn by a human performing a method using accelerometer data to classify human activities is disclosed. The method uses memory and computation efficiently. A stream of samples is divided into a sequence of sampling periods; each sample has an acceleration value for each axis (e.g., a 3-D accelerometer). Standard deviation of the values for each axis during each sampling period are calculated. A running sum of each axis' values can be maintained sample-by-sample. Each value is sorted into a bin of a histogram, by quantifying a deviance from a respective mean in standard deviations. A standard deviation produced from samples of a previous period can be used. The histogram is compared with histograms associated with particular activities and a classification output can be produced. Classification outputs from multiple sampling periods can be used for voting. A threshold amount of activity can be required to begin activity classification.

29 Claims, 5 Drawing Sheets

EFFICIENT ACTIVITY CLASSIFICATION FROM MOTION INPUTS

CROSS REFERENCE TO RELATED APPLICATIONS

This application claims priority from U.S. Provisional Patent Application No. 61/749,494, filed on Jan. 7, 2013, which is incorporated by reference in its entirety herein for all purposes.

BACKGROUND

1. Field

The following relates, in one aspect, to systems that identify an activity being performed by a human, based on motion inputs.

2. Related Art

Humans have used devices to gather data about their activities for some time. For example, bicycle computers have been used to track speed of a bicycle based on wheel RPM. Such a device can be programmed with characteristics of a rider, in order to estimate power output, calories burned and so on. More recently, devices have been equipped with Global Positioning System (GPS) receivers that allow speed and position information to be derived from outputs of the GPS receiver for any of a variety of human activities, such as running, skiing, bicycling, and so on. These activities are gross motor activities about which the kinds of information useful to the participant are relatively easily characterized and produced from such data inputs. For example, information outputs can include current and average speeds, elevation, elevation change, calories burned, and the like.

However, to characterize fine motor skill activities, more information-rich sources of information are helpful. Additionally, processing of the information from these sources may be more complex.

SUMMARY

In one aspect, a device is provided that will characterize human activity based on accelerometer inputs. In one particular aspect, the disclosure relates to using a multi-axis accelerometer embedded in a small device worn by a person to infer or otherwise categorize an activity being performed by that person. The device implements such activity classification in a way that is efficient in usage of both power consumption and memory requirements. In one example, the device is a battery powered watch.

In an example, these features are realized by providing a constant-time computation approach, in which data structures required for classification can be maintained and updated one sample at a time, in constant time per sample. This constant-time computation approach obviates a need to retain raw data in RAM. In an approach, only integer arithmetic is used, and algorithms are adapted or designed in order to work within the precision and range constraints afforded by using only integer arithmetic, rather than floating point computations. Avoiding floating point computation conserves power and minimizes memory foot print. Avoiding floating point computation also may allow implementation of the disclosed algorithm in less-expensive computation hardware.

In a still further aspect, the algorithms employed respect a storage constraint, so that they do not need to go beyond a known maximum memory usage. As such, data storage requirements of implementations do not increase with time. These and other aspects will become more apparent from the following disclosure

DETAILED DESCRIPTION

As introduced above, a small form factor device (e.g., a watch) (hereinafter, referred to as a "device" for clarity) can be worn by a person. The device includes a multi-axis accelerometer. The accelerometer produces outputs that are processed according to aspects disclosed herein. As will be explained in further detail below, there is disclosed an approach to categorizing an activity being performed by a person wearing the device in which power and memory constraints are observed. Here, "worn" can include any mechanism for attaching the device, such that motion of the person results in motion of the device. In one approach, power consumption and memory requirements are minimized, according to specific techniques. Example techniques include constant time computation, which, in an approach, includes that data structures used during activity classification can be maintained and updated one sample at a time, in constant time per sample. In such approach, retaining raw sample data in RAM can be avoided.

Additionally, the available data is processed using techniques adapted for integer arithmetic, which avoids floating point computation. Avoiding floating point computation conserves power and reduces a memory footprint required for storage of data used in such computation. The techniques also can operate within a constant amount of data storage, over time. Thus, storage requirements of the algorithm do not increase with time. In one implementation, the activity characterization processes disclosed herein can be implemented using under 2K bytes of memory.

Figure 1:
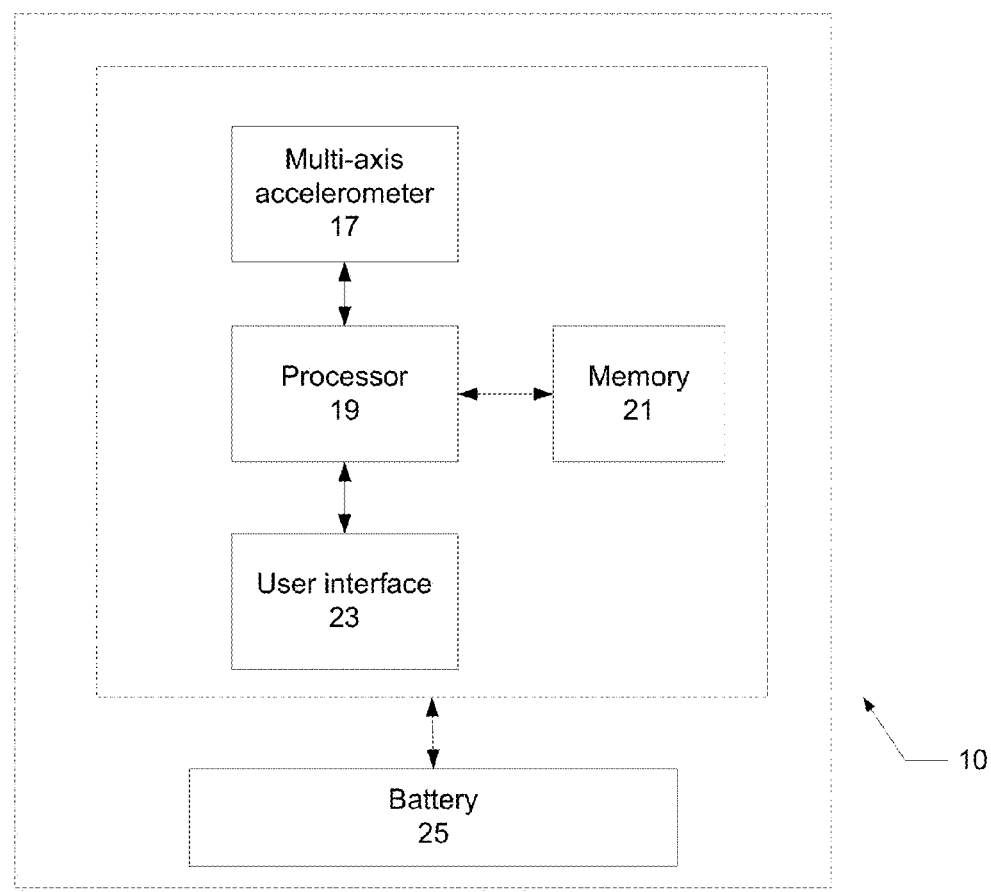
FIG. 1 depicts components of an example device in which aspects of the disclosure can be implemented.
Figure 2:
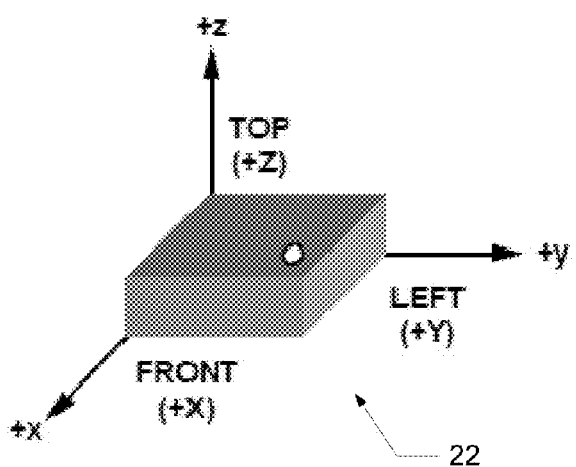
FIG. 2 depicts a 3-D coordinate system in which an accelerometer can produce samples of sensed acceleration in each of the dimensions in the 3-D coordinate system, where each sample has a value for each axis of the 3-D coordinate system, indicative of acceleration sensed along that axis.

Turning to FIG. 1, components of an example device 10 are depicted. Device 10 includes a multi-axis accelerometer 17, which is operable to sense acceleration in multiple axial directions and in one example, is operable to sense acceleration in each of 3 canonical coordinate directions. FIG. 2 depicts an example coordinate system 22 comprising an XYZ coordinate system. Such usage is by way of example and not limitation, in that acceleration in 3-D space can be characterized in a variety of ways, and the processes disclosed herein can be adapted accordingly. Accelerometer 17 can thus output a value for each dimension depicted in FIG. 2, thereby communicating whether positive or negative acceleration was detected in each coordinate direction. In this disclosure, accelerometer 17 generates samples that comprise data for different dimensions of space. For clarity, a sample thus refers to a collection of data for all sampled dimensions, for a particular moment in sampling time, and the data resulting from the sampling, for each sampled dimension is called a "value" of acceleration sensed in that particular moment, for a specific axis. Where samples are taken for each dimension of a 3-D space, each sample is a triplet of values.

A processor 19 receives samples of acceleration sensed by accelerometer 17. For example, processor 19 can receive periodic samples from accelerometer 17. In a specific example, processor 19 receives samples from accelerometer at a rate of around 100 Hertz. In an example, processor 19 can execute an interrupt routine according to a timer that maintains a sampling schedule. Processor 19 couples with a memory 21, which can be implemented as a non-transitory data storage, such as one or more of a Random Access Memory (RAM), implemented according to an appropriate technology, and a non-volatile memory, such as a flash memory. Non-volatile memory can be used for storing program information that can be used for configuring processor 19, as well as settings or parameter information as may be appropriate.

A user interface 23 couples with processor 19. User interface 23 may be composed of multiple elements, and these elements can vary with the implementation. For example, user interface 23 may comprise a visible display on which text, graphics or both text and graphics can be displayed. User interface 23 may comprise one or more buttons, or a touch screen interface. User interface 23 may comprise speech recognition as an input, and speech synthesis as an output mechanism. User interface 23 also may comprise components that are capable of communicating with device 10 over a data interface. For example, device 10 may be equipped with a Personal Area Network (PAN) capability, such as Bluetooth, and data may be retrieved from or provided to device 10 through a PAN connection. Further explanation concerning the operation and of the components of device 10 in order to implement aspects of the disclosure follows.

FIG. 2 depicts a three-space orthogonal coordinate system 22. In an example, multi-axis accelerometer 17 is sampled at Sampling Rate (SR) (e.g. 100 Hz) to provide acceleration sample triplets (X, Y, Z). These triplets are input to processes described herein. Each value (X, Y, Z) in this triplet represents a signed integer acceleration value in a respective dimension.

Figure 3:
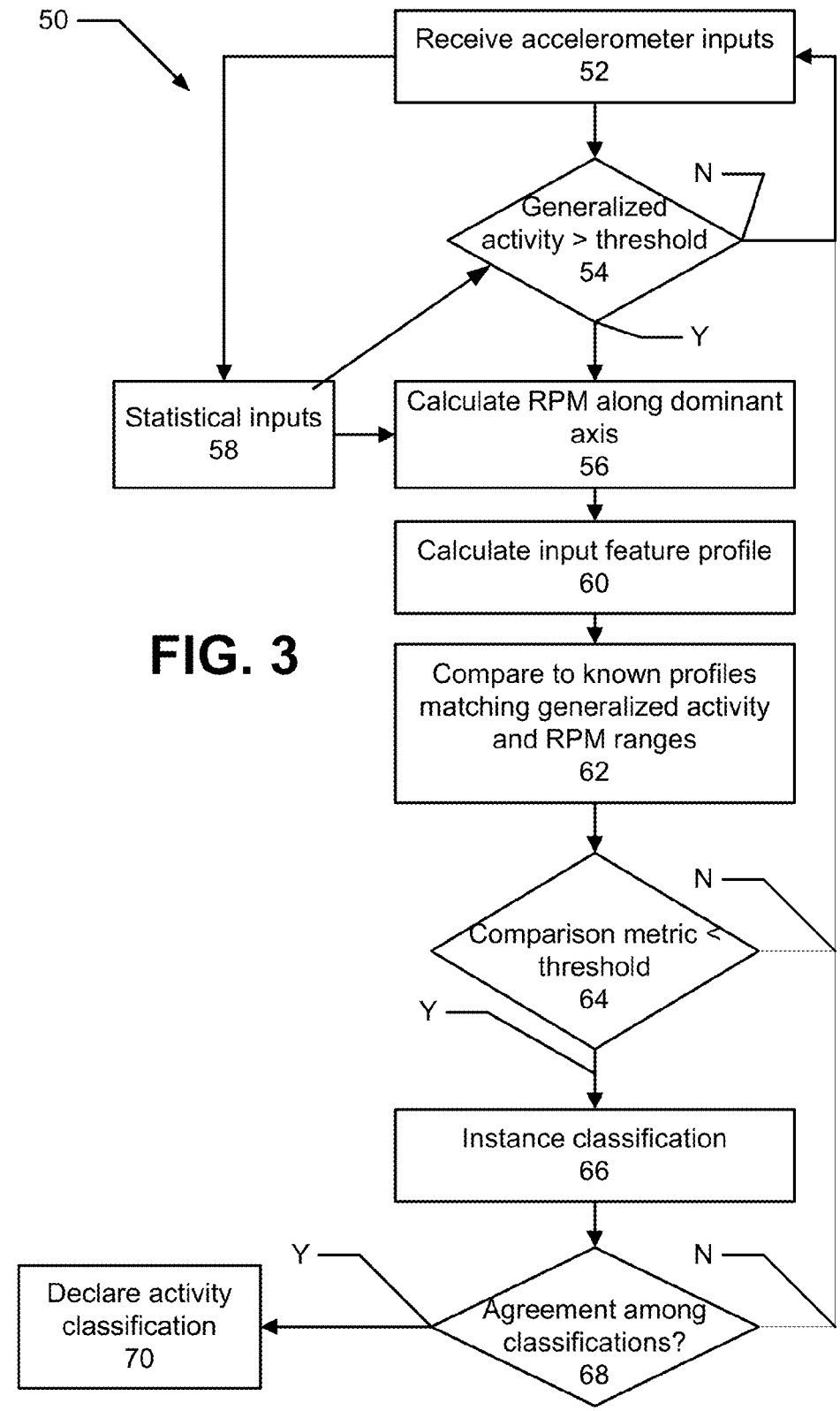
FIG. 3 depicts an example process by which the samples of acceleration can be used in classifying an activity that caused an accelerometer to generate those samples.

FIG. 3 depicts an example process 50 which is used to infer an activity being performed by a wearer of device 10. Approaches to implementing parts of process 50 are described with respect to FIGS. 4-6. At 52, accelerometer data is received. As introduced above, such accelerometer data can be realized as a stream of samples, each sample comprising a respective value for each dimension in which acceleration is sensed. For example, accelerometer 17 can be sampled at a rate of 100 times per second. In one approach, the samples of each axis are collected over a 2.56 second period (256 time points). As explained below, these sampling details allow a computationally efficient approach to performing certain calculations. However, other sampling rates and sampling periods can be provided, and these values are for a particular implementation.

At 58, statistics concerning the samples are computed. In an example, the variance and mean of the samples for one period (2.56 seconds in one example) are computed. The calculated variance and mean can be averaged with variances and means for previous sample periods. For example, in one approach, the variance and mean for a most recent sampling period respectively are averaged with the variance and mean of the previous three sampling periods. In this approach, there is a running average of four sampling periods, yielding a 10.24 second running average of the mean and standard deviation for each axis. An example approach to calculating the mean and variance is described with respect to FIG. 4.

Before beginning data processing to infer an activity being performed, at 54, a test whether a level of activity detected by device 10 is in excess of a threshold is performed. This step filters out spurious classifications, in that no classification is attempted if the generalized level of activity is too small. This test also avoids more computationally intensive data processing on accelerometer data that is unlikely to have been generated by an activity, and rather may simply be indicative of non-specific movement. In one approach, the generalized level of activity is determined by the sum of the variances in the values of the stream of sample data from accelerometer 17, for each axis. In one approach, the test is performed by computing a square root of the sum of variances in the data for the axes. If the generalized activity level is less than a threshold, then the process can return to 52 so that further accelerometer data can be collected and processed.

If the generalized activity level is greater than or equal to the threshold, then at 56, a repetitions per minute on a dominant axis of movement is calculated. In one approach, accelerometer outputs for each axis are passed through a 16-sample running average (smoothing) filter and zero crossings are counted in the running average over the sampling period (e.g., 2.56 seconds of 100 Hz sampling, leading to 256 samples). The repetitions per minute for each axis may be calculated using a length of time between zero crossings. From the three calculated repetitions per minute (one for each axis), the repetitions per minute from the axis for which the largest standard deviation was calculated (at 58) is selected as the dominant axis.

At 60, an input feature profile is calculated. An approach to implementing the calculation at 60 is described below, relative to FIGS. 6 and 7. However, before describing such example, a remainder of FIG. 3 is described. After 60, an input feature profile is available for use in activity classification.

At 62, a comparison is performed between the input feature profile and feature profiles for a selection of activities. Such feature profiles of known activities to be used in the comparison can be selected according to a measurement of generalized activity (available from 52, above), and repetitions per minute data (available from 56). Such comparison can be implemented in a variety of ways. One example algorithm is to calculate the sum of the absolute differences between histograms, with the smallest sum representing the best classification. If the sum exceeds a threshold, the activity can be classified as unknown for that sampling period.

In one approach, each feature profile is associated with a max and min for each of the generalized activity level and the repetitions per minute. If the general activity level and repetitions per minute for the current sampling period are within the max and min associated with a particular feature profile, then that feature profile is retained for further comparison.

Given a set of comparison feature profiles, the feature profile for the activity to be classified is compared with the feature profiles of the set. In one approach, each feature profile has a set of numerical characterizations that relate to different parameters or ranges of data. For each feature profile, a sum of absolute differences for each parameter between the feature profile for the activity to be classified and each comparison profile is made. Each calculation thus results in a comparison metric where a numerically larger result indicates a poorer match, and a smaller result indicates a better match. Thus, at 64, if the result is less than a threshold, then a classification of the activity is attempted and if the result is larger (or equal to) the threshold, then no classification of the activity is attempted based on the sample data in that sampling period. Of course, this approach to producing a numerical representation of closeness of data is an example, and based on the disclosure, a person of ordinary skill can devise a variety of other ways to produce data that can be used to accomplish such purpose. At 66, a classification of the activity is made. At 68, multiple classifications are compared. For example, if 3 of the last 4 classifications match, then at 70, a classification of the activity causing the accelerometer outputs is declared. Otherwise, sample data for a subsequent period is collected and the process is repeated.

An example of an input feature profile is an activity histogram, which will be described in detail below. One approach to producing an activity histogram is to use calculated mean and variance of the accelerometer data for each axis. In brief, it is determined, for each sample, how far each value is from a mean of a set of sample values for that dimension. In some implementations, the variance and standard deviation calculated from the samples of a previous period are used in producing the histogram of a subsequent sampling period. In some implementations, a mean is maintained over multiple sampling periods and the value thus can be compared with that mean in the same way. According to that comparison, the sample is allocated to a bin of a histogram. The resulting histogram can be used as a basis for characterizing an activity being performed.

Figure 4:
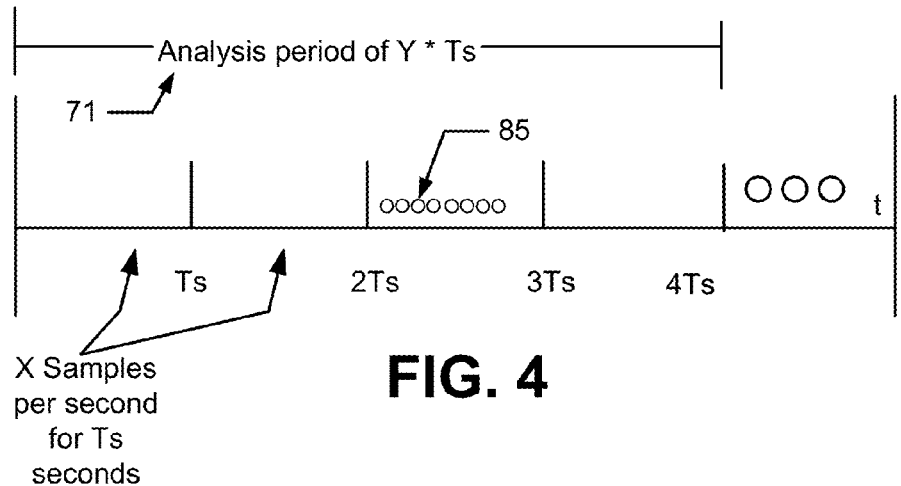
FIG. 4 depicts a timeline with sampling periods and an analysis period.
Figure 5:
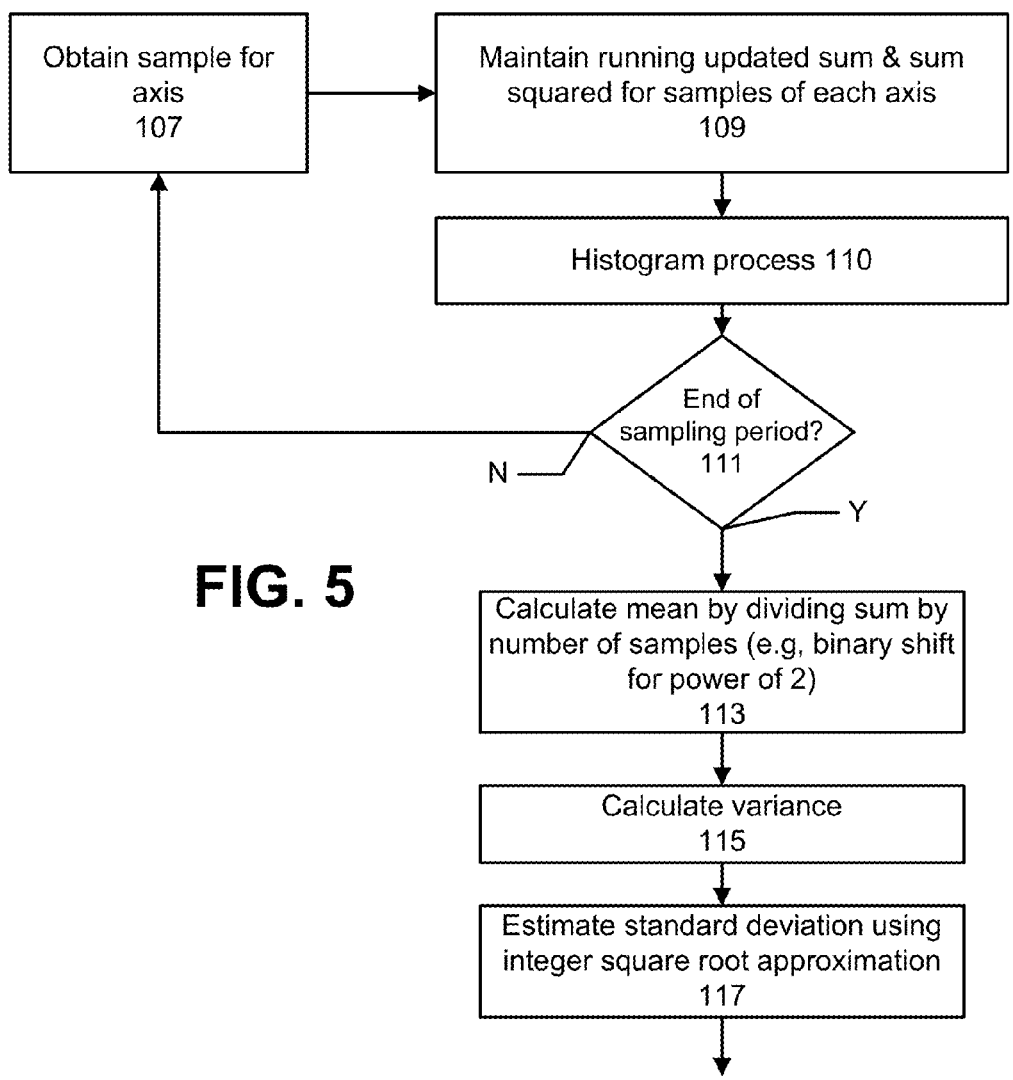
FIG. 5 depicts an example process for calculating variance and standard deviation in an implementation.

FIG. 4 depicts a timeline with sampling periods of Ts, which is in describing the process of FIG. 5. During each sampling period Ts, X samples of accelerometer data are taken. An analysis period 71 is a multiple (Y) of the sampling period Ts. Samples obtained by the accelerometer are illustrated as being received in a sequence at 85.

Figure 6:
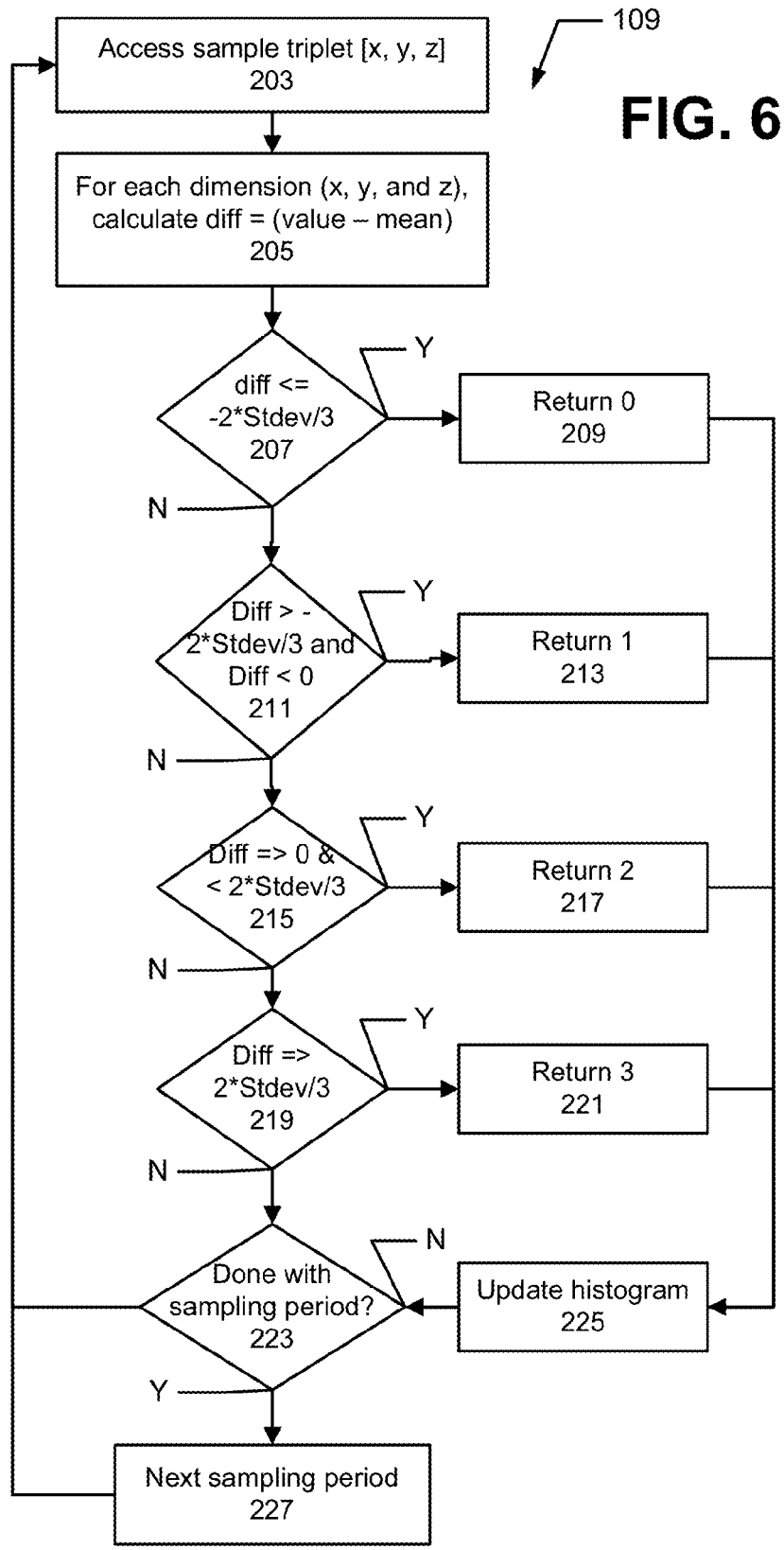
FIG. 6 depicts a process for categorizing a sample based on standard deviations of the constituent values in the sample, and creation of a histogram having counts of samples that were assigned to different bins in the histogram.

FIG. 5 depicts an example of processing the accelerometer samples (e.g., processing of the samples in the sampling period between 3Ts and 4Ts (the last sampling period in analysis period 71)). During the time period between 3Ts and 4Ts, at 107, samples taken of accelerometer are obtained as they are available, and at 109, a running sum and a square of the sum for each axis of accelerometer data is maintained. At 110, a histogram generation process is performed, an example of which is depicted in FIG. 6.

At 111, a check whether the end of the sampling period has arrived is made, and if so, then at 113, a mean is calculated for the samples of each axis based on the running sum. In one approach, each sampling period has a power of 2 number of samples, so a mean can be determined by a binary shift of the appropriate number of bits (e.g., for 256 samples, a binary shift of 8 binary digits would be performed). At 115, a variance is calculated. In one approach, variance is calculated as the square of the sum, minus the square of the sum divided by the number of samples (X), and this amount is divided by X. As an equation, $$\text{Variance} = \frac{\text{sum}_{sqr} - \text{sum} * \text{sum}/X}{X}.$$

At 117, the standard deviation is defined as square root of the variance. Performing a true square root is computationally expensive. In one approach, the standard deviation is estimated by using an integer square root approximation technique. At 119, the resulting mean and variance is averaged with the mean and variance of a previous Y sampling periods (making up analysis period 71). In one example, analysis period 71 is four sampling periods (i.e., 4*Ts). Here, for simplicity, approximations of the standard deviation are referred to simply as standard deviation, even though such approximations may not result in an exact standard deviation. Additionally, standard deviation is an example for developing an expression of how dispersed a set of samples are, around a mean, and as such, express a likelihood of a given value being within a particular distance from the mean. As such, standard deviation is an example, standing for the more general functional purpose.

In one implementation, the square root of variance is estimated using the pseudo-code in Table 1 below:

TABLE 1

```
int intSqrt(int val) {
    int temp, g=0, b = 32768, bshift = 15;
    do {
        temp = (((g << 1) + b)<<bshift--);
        if (val >= temp) {
            g += b;
            val -= temp;
        }
        b = b >> 1;
    } while (b > 0);
        return g;
}
```

Figure 7:
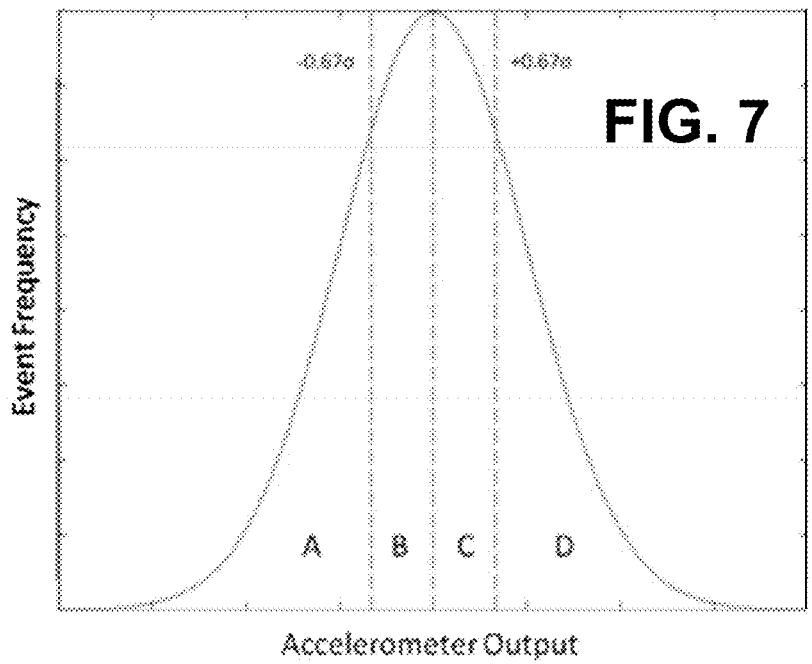
FIG. 7 depicts a value in a sample being allocated to one of four categories, according to its distance from a mean of the values in the axis for that value, expressed in terms of a difference (quantified in standard deviations or portions thereof) between values for that axis in the sampling period and a mean of the values.

FIG. 6 depicts an example of how a histogram can be produced for samples of a sampling period. In an example, in order to allocate each sample to a bin of the histogram, each value in each sample is processed to produce a selection of one of four possible values based on how many standard deviations (or portion thereof) it is from a mean of that dimension, for that sampling period. FIG. 7 depicts a curve divided into four regions (regions A,B,C,D). The set of four possible values can be represented by a two bit number, so that an output of this portion of the processing is a 2 bit value representing how far from a mean that sample is.

Returning to FIG. 6, an example process according to this approach includes that, at 203, a sample from accelerometer is accessed (this access can be subsumed in the obtaining 107 of FIG. 5). In accordance with the example, the sample includes a triplet of values, with one value for each of 3 axes (dimensions). The process depicted in FIG. 5 is performed for each axis of each sample. At 205, for each axis, a difference between a value in the triplet and a mean of values for that axis is calculated ("cliff" in FIG. 5). In one example, the mean used is a mean calculated for values from samples received in one or more prior sampling periods. In one example, an average of values received in the previous four sampling periods is used. The approach of using values from one or more previous sampling periods provides a stable mean, for calculating these differences while the samples of a current sampling period are being received.

The difference is characterized. In an example, if the difference is in Region A (see FIG. 7), which is mathematically represented as an area of the curve less than or equal to −⅔ of a standard deviation from the mean, then at 209, 0 is assigned for that axis of that sample. If the difference is in Region B, which is mathematically represented as an area of the curve that is between Region A and the mean, then 1 is assigned for that axis of that sample. If the difference is in Region C, which is mathematically represented as an area of the curve that is between the mean and ⅔ of a standard deviation greater than the mean, then a 2 is assigned for that axis for that sample. If the difference is in Region C, which is mathematically represented as an area of the curve that is greater than or equal to ⅔ of a standard deviation from the mean, then a 3 is assigned for that axis for that sample.

Since a value between 0 and 3 is assigned for each value of each sample, there are 3 different values between 0 and 3 for each triplet. Each 0-3 value can be represented by 2 bits of a binary number, and collectively, all 3 values can be represented by 6 bits. 6 bits can index 64 unique bins of a histogram. In one implementation, the 2 bit values for each dimension are combined into an index for indexing a 64 bin histogram according to the formula Index=x+4*y+16*z, where x, y, and z represent the 0-3 value for different axes of the accelerometer. For each sample, this index is used to increment the bin in the 64 bin histogram identified by that index.

Stated otherwise, since there are three axes represented in a triplet, the processing for each triplet results in six total bits. These six bits collectively can represent 64 unique values (2^6). Each of these 64 values can be used as an address of a bin in a 64 bin histogram. A separate histogram is created for each sampling period. Each time a triplet is mapped to a particular bin of the 64-bin histogram for the sampling period in which that triplet was obtained. A number associated with that bin is incremented. In one implementation, there is a constant number of samples in each sampling period. In such an implementation, each sampling period will have the same number of data points. Because a single bin, of the 64 available bins, is incremented for each of the triplets, the sum of all the numbers associated with each bin of the histogram will be a constant at the completion of each sampling period (e.g., each completed histogram will include 256 total samples, allocated among 64 different bins). Therefore, each of the histograms is normalized automatically, and no separate normalization of different histograms needs to be done in such implementation.

Thus, each sample is characterized according to how different its constituent values are from a respective mean of values for the respective axis to which each value pertains. The mean can be calculated from a set of previously-received samples, and can be a mean from a window of a previous 4 sampling periods, in an example. Collectively, these differences are used to produce a histogram that counts each sample. The produced histogram can be compared with histograms that are associated with or otherwise known to be correlated with specific activities.

Training is done by generating a library of histograms for known activities. Activity classification is accomplished by comparing the measured histogram to the histograms in the training library. In one implementation, one histogram library can be created that is used for all individuals, such that individual modifications or customizations are unnecessary. However, customization of these histograms for specific users can be implemented. For example, device 10 can provide a training mode in which a user selects an activity that will be performed, and the device generates data that will be used in future classification processes. To generate the library of histograms, a device can be worn in a specific place or configuration or using a specific attachment mechanism that replicates use conditions. For example, where the device is a watch, it can be worn as a watch on a wrist during performance of that activity.

In some implementations of these disclosures, all calculations are integer arithmetic. Most calculations are done using 16 bit integer arithmetic. A few calculations are done using 32 bit integers. By using only integers, power consumption and the memory size requirements are reduced, compared with using floating point arithmetic. In one example, the processes to implement activity classification according to the disclosure can be realized in 2 k bytes of RAM.

Figure 8:
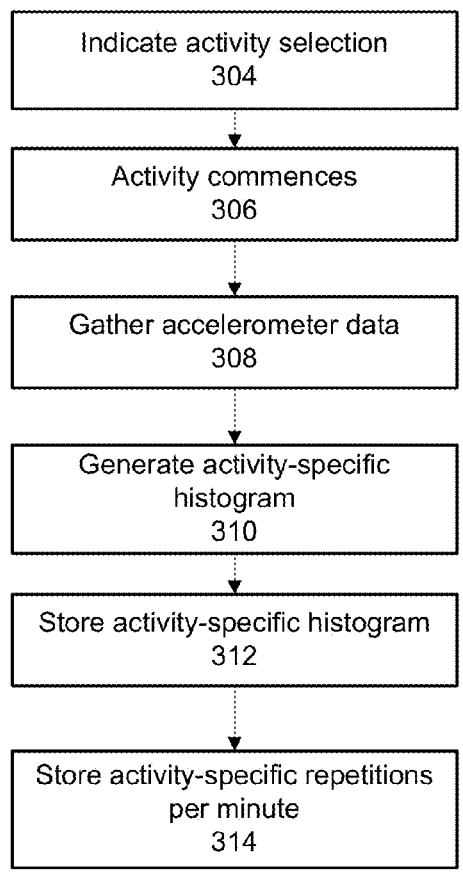
FIG. 8 depicts a process for developing data used in processes that implement aspects of the disclosure.

FIG. 8 depicts a process by which activity histograms and other classification data can be produced or maintained for use in, classification processes according to the disclosure. At 304, an activity to be trained can be indicated. At 306, the activity commences (e.g., a user wearing the device can begin the activity). At 308, accelerometer outputs are gathered. At 310, a method according to the disclosure is employed to produce an activity-specific histogram, which is stored for later comparison with histograms generated from unknown activities that are to be classified. In some approaches, the histograms generated according to the process of FIG. 7 can be generated and stored (at 312) on the device by a manufacturer of the device, where those histograms are not personalized for a particular user. At 314, the activity-specific repetitions per minute also can be stored. In some examples, a user can use the process of FIG. 8 to train a device for personal use. In some examples, activity histograms can be generated and stored on the device (not personalized to a user), and those histograms can be customized or updated during training by a specific user.

Other kinds of data that can be captured or maintained for each activity includes an estimate of maximum and minimum standard deviation for samples on each axis when the activity is performed, and an estimated value or range of values for repetitions per minute on each axis or on a dominant axis are stored. These characterizations of each activity can be used in implementations of the process of FIG. 3.

The disclosure describes various calculations, production of values for specified variables, such as mean, variance and standard deviation, and other computation to be performed. It would be understood from the disclosure that such computation is performed according to and results in outputs according to a precision in which the calculations are performed. Thus, embodiments need not produce an exact mean, variance or standard deviation, for example, in order to be practicing the invention.

This disclosure provides an example of a power and memory efficient approach to classifying an activity being performed by a moving body, such as a robot or a living creature (e.g., a human), based on acceleration data obtained from a multi-axis accelerometer. examples of A variety of implementations can be realized according to the example. Specific examples of parameters, sampling rates, sampling periods, a resolution of activity histograms were all explained; however, other implementations can vary these details. For example, a sampling rate may be made higher or a sampling period longer. These changes may have effects on the outputs realized by practicing the disclosed processes, which can be considered in the overall design of a device according to the disclosure. Such variations and details would be understood by a person of ordinary skill from the disclosure.

The order of activities depicted in the diagrams is not by way of limitation that such activities must be, or are preferred to be performed in that order. These relative arrangements and numbering is not an implicit disclosure of any specific limitation on ordering or arrangement of elements and steps in the claims. Process limitations may be interchanged sequentially without departing from the scope of the disclosure, and means-plus-function clauses in the claims are intended to cover the structures described as performing the recited function that include not only structural equivalents, but also equivalent structures.

As would be apparent from the disclosure, some of the components, logical blocks, modules, circuits, and algorithm steps, and other functionality disclosed may be implemented in hardware, software, firmware, or any combination thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

If implemented in firmware and/or software, the functions may be stored as one or more instructions or code on a computer-readable medium, in one example, the media is non-transitory. Examples include a computer-readable medium encoded with a data structure and a computer-readable medium encoded with a computer program. Machine-readable media includes non-transitory machine readable media. Other kinds of media include transmission media. A non-transitory medium may be any tangible medium that can be accessed by a machine. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a machine.

We claim:

1. A method of classifying an activity being performed by a moving body, comprising:
   receiving a stream of samples of acceleration data from a three-axis accelerometer worn by the moving body, each sample comprising a value for each of the three axes;
   establishing a sequence of sampling periods, each having a plurality of samples from the stream;
   maintaining a mean of at least a portion of the values for each axis;
   sorting the samples received during each of the sampling periods into an activity histogram for that sampling period, the activity histogram comprising a plurality of bins, the sorting comprising
      for each of the values of that sample, characterizing a respective difference between that value, and the mean for values of that axis,
      and selecting a bin of the plurality of bins of the activity histogram for each sample according to the characterized differences for the values of that sample; and
   outputting an activity classification by comparing the activity histogram with activity histograms associated with classified activities.

2. The method of classifying an activity being performed by a moving body of claim 1, wherein the maintaining comprising calculating a respective mean for each of a plurality of sampling periods.

3. The method of classifying an activity being performed by a moving body of claim 1, further comprising producing a repetitions frequency for each axis, and comparing the produced repetitions frequency to stored repetitions frequencies associated with the classified activities.

4. The method of classifying an activity being performed by a moving body of claim 1, wherein the maintaining comprising calculating a respective mean for the values of each axis in a moving window of sampling periods, and using those means for the characterizing of the differences of values in a subsequent sampling period.

5. The method of classifying an activity being performed by a moving body of claim 4, further comprising maintaining a running sum of the values received during a current sampling period and calculating a mean of the values for the current sampling period and updating the mean for the moving window of sampling periods.

6. The method of classifying an activity being performed by a moving body of claim 1, further comprising maintaining a running sum of the values received during each sampling period, discarding the original values after performing the sorting, and using the running sum to calculate respective means for the values of each axis during the sampling period.

7. The method of classifying an activity being performed by a moving body of claim 1, wherein the difference for each value is taken with respect to respective means of the values for each axis received during one or more previous sampling periods.

8. The method of classifying an activity being performed by a moving body of claim 1, further comprising calculating a standard deviation for the values of each axis during each sampling period, and using the standard deviation for the values of one or more previous sampling periods in the characterizing of the differences of the values for each axis.

9. The method of classifying an activity being performed by a moving body of claim 8, further comprising maintaining a running sum of the values received during each sampling period and discarding the original values after performing the sorting.

10. The method of classifying an activity being performed by a moving body of claim 1, further comprising conditioning the performance of one or more portions of the method on detecting a general level of activity in excess of a threshold level.

11. The method of classifying an activity being performed by a moving body of claim 1, wherein the respective mean for the values of each axis is calculated from 1024 samples previous to the samples being received for a current sampling period.

12. The method of classifying an activity being performed by a moving body of claim 1, wherein each sampling period comprises 256 samples.

13. The method of classifying an activity being performed by a moving body of claim 1, wherein a rate at which samples are produced is 100 Hz.

14. The method of classifying an activity being performed by a moving body of claim 1, wherein the method is performed using only integer calculations.

15. The method of classifying an activity being performed by a moving body of claim 1, wherein the sorting of the sampling comprises relatively weighting the values for each axis.

16. The method of classifying an activity being performed by a moving body of claim 15, wherein the three-axis accelerometer comprises a vertical axis, and the value for the vertical axis is weighted more heavily than values for the remaining axes.

17. The method of classifying an activity being performed by a moving body of claim 1, wherein the sorting comprises assigning each value into one of n positions, and the activity histogram has n^3 bins, and each sample is assigned a bin by a weighted combination of the positions for the constituent values of that sample.

18. The method of classifying an activity being performed by a moving body of claim 17, further comprising incrementing a per-bin count and using the counts of each bin as the activity histogram.

19. The method of classifying an activity being performed by a moving body of claim 1, the selecting of the bin for each sample comprises using a respective standard deviation of previously-received values for each axis to classify a current value into one of four categories, a first category being more negative than ⅔ of a standard deviation from the mean, a second category being between the mean and −⅔ of a standard deviation from the mean, a third category being between the mean and ⅔ of a standard deviation from the mean and a fourth category being farther from the mean than ⅔ of a standard deviation.

20. A device to be worn by a moving body to produce classifications of activities being performed by that creature, comprising:
  a multi-axis accelerometer;
  a non-transitory memory;
  a processor coupled to receive samples, at a sampling rate, of acceleration sensed by the multi-axis accelerometer, each sample comprising a value for each sampled axis, the processor configured to perform a method comprising:
    maintaining, for each axis of accelerometer data, a respective current sum and a square of the current sum of the values received during a sampling period for that axis,
    estimating a respective standard deviation for the values of each axis during each sampling period;
    sorting each sample into one bin of a histogram having n^3 bins, by sorting the per-axis values of that sample into one of n categories, the sorting comprising characterizing an amount of difference between each value of that sample with a mean of previously-received sample values for that axis, the characterizing expressed as a factor of the standard deviation of the values for that axis;
    incrementing a per-bin count for each sample sorted into that bin;
    comparing the histogram with a set of histograms that have been determined to be indicative of different activities, and
    outputting a classification of the activity being performed during the sampling period based on a result of the comparing.

21. The device of claim 20, wherein the estimating of the standard deviation comprises using an integer approximation of a square root of a calculated variance to estimate a standard deviation.

22. The device of claim 21, wherein the method further comprises using the standard deviation for each value to classify that value into one of four categories, the multi-axis accelerometer produces values for each of three axes, and the histogram comprises 64 bins.

23. The device of claim 21, wherein the selecting comprises using the standard deviation for each value to classify that value into one of four categories, a first category being more negative than ⅔ of a standard deviation from the mean, a second category being between the mean and −⅔ of a standard deviation from the mean, a third category being between the mean and ⅔ of a standard deviation from the mean and a fourth category being farther from the mean than ⅔ of a standard deviation.

24. The device of claim 21, wherein the non-transitory memory is sized to store samples for a single sampling period, and samples for a subsequent sampling period overwrite samples for a previous sampling period in the non-transitory memory when stored.

25. The device of claim 21, wherein the processor is configured to perform the method conditionally upon a generalized level of activity sensed by the accelerometer being greater than a threshold level of activity.

26. The device of claim 21, wherein the processor is configured to perform the method in response to a generalized level of activity sensed by the accelerometer being greater than a threshold level of activity.

27. The device of claim 21, wherein the method which the processor is configured to perform further comprises selecting the set of histograms from available comparison histograms by matching a repetitions per minute calculated for a dominant axis of movement in the accelerometer data with repetitions per minute figures stored with the available comparison histograms.

28. The device of claim 21, wherein the non-transitory memory stores the set of histograms, which are generic among possible users of the device.

29. A non-transitory machine readable medium, the medium storing machine executable instructions for configuring a machine to perform a method of classifying an activity being performed by a moving body, comprising:
  receiving a stream of samples of acceleration data from a three-axis accelerometer worn by the moving body, each sample comprising a value for each of the three axes;
  establishing a sequence of sampling periods, each having a plurality of samples from the stream;
  maintaining a mean of at least a portion of the values for each axis;
  sorting the samples received during each of the sampling periods into an activity histogram for that sampling period, the activity histogram comprising a plurality of bins, the sorting comprising
    for each of the values of that sample, characterizing a respective difference between that value, and the mean for values of that axis,
    and selecting a bin of the plurality of bins of the activity histogram for each sample according to the characterized differences for the values of that sample; and
  outputting an activity classification by comparing the activity histogram with activity histograms.

* * * * *